(12) United States Patent
Pastore et al.

(10) Patent No.: US 7,217,296 B2
(45) Date of Patent: *May 15, 2007

(54) DYEING COMPOSITION WITH A LIGHTENING EFFECT FOR HUMAN KERATIN MATERIALS COMPRISING AT LEAST ONE FLUORESCENT DYE

(75) Inventors: Florent Pastore, Rueil Malmaison (FR); Luc Gourlaouen, Asnière (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/490,869

(22) PCT Filed: Sep. 24, 2002

(86) PCT No.: PCT/FR02/03252

§ 371 (c)(1), (2), (4) Date: Oct. 5, 2004

(87) PCT Pub. No.: WO03/028685

PCT Pub. Date: Apr. 10, 2003

(65) Prior Publication Data

US 2005/0028301 A1  Feb. 10, 2005

(30) Foreign Application Priority Data

Sep. 28, 2001  (FR) .................................. 01 12525

(51) Int. Cl.
*A61K 7/13* (2006.01)
(52) U.S. Cl. .................. 8/405; 8/406; 8/407; 8/410; 8/411; 8/421; 8/648; 132/202; 132/208
(58) Field of Classification Search .................. 8/405, 8/406, 407, 410, 411, 421, 648; 132/202, 132/208
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Ditmar | |
| 2,375,853 A | 5/1945 | Kirby et al. | |
| 2,388,614 A | 11/1945 | Kirby et al. | |
| 2,454,547 A | 11/1948 | Bock et al. | |
| 2,798,053 A | 7/1957 | Brown | |
| 2,851,424 A | 9/1958 | Switzer et al. | |
| 2,923,692 A | 2/1960 | Ackerman et al. | |
| 2,961,347 A | 11/1960 | Floyd | |
| 2,979,465 A | 4/1961 | Parran et al. | |
| 3,014,041 A | 12/1961 | Hausermann et al. | |
| 3,206,462 A | 9/1965 | McCarty | |
| 3,227,615 A | 1/1966 | Korden | |
| 3,472,840 A | 10/1969 | Stone et al. | |
| 3,632,559 A | 1/1972 | Matter et al. | |
| 3,639,127 A | 2/1972 | Brooker et al. | |
| 3,658,985 A | 4/1972 | Olson, Jr. et al. | |
| 3,856,550 A | 12/1974 | Bens et al. | |
| 3,874,870 A | 4/1975 | Green et al. | |
| 3,910,862 A | 10/1975 | Barabas et al. | |
| 3,912,808 A | 10/1975 | Sokol | |
| 3,915,921 A | 10/1975 | Schlatzer, Jr. | |
| 3,917,817 A | 11/1975 | Vanlerberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,005,193 A | 1/1977 | Green et al. | |
| 4,013,787 A | 3/1977 | Vanlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,020 A | 5/1977 | Green et al. | |
| 4,031,307 A | 6/1977 | DeMartino et al. | |
| 4,075,136 A | 2/1978 | Schaper | |
| 4,131,576 A | 12/1978 | Iovine et al. | |
| 4,157,388 A | 6/1979 | Christiansen | |
| 4,165,367 A | 8/1979 | Chakrabarti | |
| 4,166,894 A | 9/1979 | Schaper | |
| 4,172,887 A | 10/1979 | Vanlerberghe et al. | |
| 4,185,087 A | 1/1980 | Morlino | |

(Continued)

FOREIGN PATENT DOCUMENTS

AT   302 534   10/1972

(Continued)

OTHER PUBLICATIONS

CAS Abstract for JP 2000-136340—Chemical Abstracts Service; Database Accession No. 2000: 317079; XP-002269220, JP 2000136340 (Pentel Co., Ltd.), May 16, 2000.

(Continued)

*Primary Examiner*—Eisa Elhilo
(74) *Attorney, Agent, or Firm*—Finnegan, Henderson, Farabow, Garrett & Dunner L.L.P.

(57) ABSTRACT

The invention relates to a cosmetic dyeing composition that is used to lighten human keratinous matter and, more specifically, artificially colored or pigmented hair and dark skin. The inventive composition comprises at least one flourescent dye. The invention also relates to the methods using said composition.

34 Claims, No Drawings

U.S. PATENT DOCUMENTS

| | | | |
|---|---|---|---|
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,237,243 A | 12/1980 | Quack et al. |
| 4,240,450 A | 12/1980 | Grollier et al. |
| 4,256,458 A | 3/1981 | Degen et al. |
| 4,277,581 A | 7/1981 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,509,949 A | 4/1985 | Huang et al. |
| 4,591,610 A | 5/1986 | Grollier |
| 4,608,250 A | 8/1986 | Jacquet et al. |
| 4,693,935 A | 9/1987 | Mazurek |
| 4,702,906 A | 10/1987 | Jacquet et al. |
| 4,719,099 A | 1/1988 | Grollier et al. |
| 4,719,282 A | 1/1988 | Nadolsky et al. |
| 4,728,571 A | 3/1988 | Clemens et al. |
| 4,761,273 A | 8/1988 | Grollier et al. |
| 4,781,724 A | 11/1988 | Wajaroff et al. |
| 4,823,985 A | 4/1989 | Grollier et al. |
| 4,839,166 A | 6/1989 | Grollier et al. |
| 4,948,579 A | 8/1990 | Jacquet et al. |
| 4,961,925 A | 10/1990 | Tsujino et al. |
| 4,972,037 A | 11/1990 | Garbe et al. |
| 4,996,059 A | 2/1991 | Grollier et al. |
| 5,009,880 A | 4/1991 | Grollier et al. |
| 5,089,252 A | 2/1992 | Grollier et al. |
| 5,139,037 A | 8/1992 | Grollier et al. |
| 5,188,639 A | 2/1993 | Schultz et al. ................. 8/405 |
| 5,196,189 A | 3/1993 | Jacquet et al. |
| 5,356,438 A | 10/1994 | Kim et al. .................... 8/408 |
| 5,445,655 A | 8/1995 | Kuhn et al. |
| 5,635,461 A | 6/1997 | Onitsuka et al. |
| 5,708,151 A | 1/1998 | Möckli |
| 5,744,127 A * | 4/1998 | Giuseppe et al. ............. 424/59 |
| 5,792,221 A | 8/1998 | Lagrange et al. |
| 5,830,446 A | 11/1998 | Berthiaume et al. |
| 5,833,997 A | 11/1998 | Mahieu et al. |
| 5,873,494 A | 2/1999 | Dallas, Jr. |
| 5,958,392 A | 9/1999 | Grollier et al. |
| 5,962,522 A | 10/1999 | Wacher et al. |
| 6,106,577 A | 8/2000 | Audousset et al. |
| 6,120,780 A | 9/2000 | Dupuis et al. |
| 6,180,666 B1 | 1/2001 | Wacher et al. |
| 6,260,556 B1 | 7/2001 | Legrand et al. |
| 6,391,062 B1 * | 5/2002 | Vandenbossche et al. ...... 8/405 |
| 6,436,151 B2 | 8/2002 | Cottard et al. |
| 6,436,153 B2 | 8/2002 | Rondeau |
| 6,475,248 B2 | 11/2002 | Ohashi et al. |
| 6,592,630 B2 | 7/2003 | Matsunaga et al. |
| 6,616,709 B2 | 9/2003 | Ohashi et al. |
| 6,712,861 B2 | 3/2004 | Rondeau |
| 2001/0010812 A1 | 8/2001 | Chevalier et al. |
| 2001/0023514 A1 | 9/2001 | Cottard et al. |
| 2001/0023515 A1 | 9/2001 | Cottard et al. |
| 2001/0031270 A1 | 10/2001 | Douin et al. |
| 2001/0054206 A1* | 12/2001 | Matsunaga et al. ............ 8/405 |
| 2001/0055580 A1 | 12/2001 | Belli et al. |
| 2002/0004956 A1 | 1/2002 | Rondeau |
| 2002/0012681 A1 | 1/2002 | George et al. |
| 2002/0026676 A1 | 3/2002 | Ohashi et al. |
| 2002/0046431 A1 | 4/2002 | Laurent et al. |
| 2002/0046432 A1 | 4/2002 | Rondeau |
| 2002/0088063 A1 | 7/2002 | Ohashi et al. |
| 2002/0131941 A1 | 9/2002 | Habeck et al. |
| 2002/0176836 A9 | 11/2002 | Belli et al. |
| 2002/0176875 A9 | 11/2002 | Douin et al. |
| 2003/0000023 A9 | 1/2003 | Rondeau |
| 2003/0019052 A1 | 1/2003 | Pratt |
| 2003/0019053 A9 | 1/2003 | Rondeau |
| 2003/0074747 A1 | 4/2003 | Vuarier et al. |
| 2003/0124079 A1 | 7/2003 | Mougin et al. |
| 2003/0131424 A1 | 7/2003 | Audousset et al. |
| 2004/0019981 A1 | 2/2004 | Cottard et al. |
| 2004/0034945 A1 | 2/2004 | Javet et al. |
| 2004/0037796 A1 | 2/2004 | Cottard et al. |
| 2004/0049860 A1 | 3/2004 | Cottard et al. |
| 2004/0141943 A1 | 7/2004 | Mougin et al. |
| 2004/0148711 A1 | 8/2004 | Rondeau |
| 2004/0205901 A1 | 10/2004 | Cottard et al. |
| 2005/0005368 A1 | 1/2005 | Plos et al. |
| 2005/0005369 A1 | 1/2005 | Plos et al. |
| 2005/0028301 A1 | 2/2005 | Pastore |
| 2005/0144741 A1 | 7/2005 | Lang et al. |

FOREIGN PATENT DOCUMENTS

| | | |
|---|---|---|
| CA | 1255603 | 6/1989 |
| CH | 487 231 | 3/1970 |
| DE | 33 133 32 | 10/1984 |
| DE | 196 46 804 A1 | 5/1997 |
| DE | 199 23 438 A1 | 11/2000 |
| DE | 1 99 26 377 | 12/2000 |
| DE | 1 00 29 441 | 1/2002 |
| DE | 101 41 683 A1 | 6/2003 |
| DE | 101 48 844 A1 | 10/2003 |
| EP | 0 087 060 B1 | 8/1983 |
| EP | 0 095 238 A2 | 11/1983 |
| EP | 0 080 976 B1 | 9/1986 |
| EP | 0 173 109 | 10/1989 |
| EP | 0 370 470 A2 | 5/1990 |
| EP | 0 412 704 B1 | 2/1991 |
| EP | 0 412 707 B1 | 2/1991 |
| EP | 0 445 342 A1 | 9/1991 |
| EP | 0 486 135 B1 | 5/1992 |
| EP | 0 122 324 B2 | 2/1993 |
| EP | 0 337 354 B1 | 2/1994 |
| EP | 0 582 152 B1 | 2/1994 |
| EP | 0 395 282 | 3/1995 |
| EP | 0 503 853 | 5/1996 |
| EP | 0 714 954 A2 | 6/1996 |
| EP | 0 733 355 A2 | 9/1996 |
| EP | 0 808 150 | 11/1997 |
| EP | 0 815 828 B1 | 6/1999 |
| EP | 0 970 684 A1 | 1/2000 |
| EP | 1 023 891 B1 | 8/2000 |
| EP | 1 099 437 | 5/2001 |
| EP | 1 132 076 A1 | 9/2001 |
| EP | 1 133 977 A2 | 9/2001 |
| EP | 1 191 041 A2 | 3/2002 |
| FR | 1492597 | 9/1966 |
| FR | 1583363 | 10/1969 |
| FR | 2077143 | 10/1971 |
| FR | 2080759 | 11/1971 |
| FR | 2103210 | 7/1972 |
| FR | 2162025 | 7/1973 |
| FR | 2190406 | 2/1974 |
| FR | 2252840 | 6/1975 |
| FR | 2270846 | 12/1975 |
| FR | 2280361 | 2/1976 |
| FR | 2316271 | 1/1977 |
| FR | 2320330 | 3/1977 |
| FR | 2336434 | 7/1977 |
| FR | 2368508 | 5/1978 |
| FR | 2383660 | 10/1978 |
| FR | 2393573 | 1/1979 |
| FR | 2411219 | 7/1979 |
| FR | 2416723 | 9/1979 |
| FR | 2470596 | 6/1981 |
| FR | 2505348 | 11/1982 |
| FR | 2519863 | 7/1983 |
| FR | 2542997 | 9/1984 |

| | | |
|---|---|---|
| FR | 2586913 | 3/1987 |
| FR | 2589476 | 5/1987 |
| FR | 2598611 | 11/1987 |
| FR | 2692572 | 6/1992 |
| FR | 2741261 | 5/1997 |
| FR | 2797877 | 3/2001 |
| FR | 2800612 | 5/2001 |
| FR | 2811993 | 1/2002 |
| FR | 2820032 | 8/2002 |
| FR | 2830189 | 4/2003 |
| GB | 746864 | 3/1956 |
| GB | 759385 | 10/1956 |
| GB | 1214394 | 1/1970 |
| GB | 1546809 | 5/1979 |
| GB | 1554331 | 10/1979 |
| JP | 48-17362 | 5/1973 |
| JP | 54-86521 | 7/1979 |
| JP | 2-200612 | 8/1990 |
| JP | 6-128128 | 5/1994 |
| JP | 6-183935 | 7/1994 |
| JP | 6-227954 | 8/1994 |
| JP | 8-183716 | 7/1996 |
| JP | 8-208448 | 8/1996 |
| JP | 8-259426 | 10/1996 |
| JP | 10-23629 | 9/1998 |
| JP | 11-021214 | 1/1999 |
| JP | 11-60453 | 3/1999 |
| JP | 11-343218 | 12/1999 |
| JP | 2000-01417 | 1/2000 |
| JP | 2000-86472 | 3/2000 |
| JP | 2000-505841 | 5/2000 |
| JP | 2001-172120 | 6/2001 |
| JP | 2001-220330 | 8/2001 |
| JP | 2001-226217 | 8/2001 |
| JP | 2001-261534 | 9/2001 |
| JP | 2001-261536 | 9/2001 |
| JP | 2001-294519 | 10/2001 |
| JP | 2001-516701 | 10/2001 |
| JP | 2001-516706 | 10/2001 |
| JP | 2001-516707 | 10/2001 |
| JP | 2002-12523 | 1/2002 |
| JP | 2002-12530 | 1/2002 |
| JP | 2002-47151 | 2/2002 |
| JP | 2002-226338 | 8/2002 |
| JP | 2002-249419 | 9/2002 |
| JP | 2003-55177 | 2/2003 |
| JP | 2004-059468 | 2/2004 |
| WO | WO 93/11103 | 6/1993 |
| WO | WO 93/23009 | 11/1993 |
| WO | WO 93/23446 | 11/1993 |
| WO | WO 94/02022 | 2/1994 |
| WO | WO 95/00578 | 1/1995 |
| WO | WO 95/01772 | 1/1995 |
| WO | WO 95/15144 | 6/1995 |
| WO | WO 97/18795 | 5/1997 |
| WO | WO 99/12846 | 3/1999 |
| WO | WO 99/13822 | 3/1999 |
| WO | WO 99/13823 | 3/1999 |
| WO | WO 99/13824 | 3/1999 |
| WO | WO 99/13828 | 3/1999 |
| WO | WO 99/13841 | 3/1999 |
| WO | WO 99/13845 | 3/1999 |
| WO | WO 99/13846 | 3/1999 |
| WO | WO 99/13847 | 3/1999 |
| WO | WO 99/13849 | 3/1999 |
| WO | WO 99/20235 A1 | 4/1999 |
| WO | WO 00/68282 | 11/2000 |
| WO | WO 00/71085 A2 | 11/2000 |
| WO | WO 01/43714 A1 | 6/2001 |
| WO | WO 01/62759 | 8/2001 |
| WO | WO 01/78669 | 10/2001 |
| WO | WO 02/32386 A2 | 4/2002 |
| WO | WO 02/38115 A1 | 5/2002 |
| WO | WO 02/39964 A1 | 5/2002 |
| WO | WO 02/45673 A2 | 6/2002 |
| WO | WO 02/058646 A1 | 8/2002 |
| WO | WO 02/058647 A1 | 8/2002 |
| WO | WO 02/074270 | 9/2002 |
| WO | WO 03/022232 A2 | 3/2003 |
| WO | WO 03/028685 A1 | 4/2003 |
| WO | WO 03/029359 | 4/2003 |

OTHER PUBLICATIONS

Co-pending U.S. Appl. No. 10/814,334, filed Apr. 1, 2004.
Co-pending U.S. Appl. No. 10/814,333, filed Apr. 1, 2004.
Co-pending U.S. Appl. No. 10/814,430, filed Apr. 1, 2004.
Co-pending U.S. Appl. No. 10/814,305, filed Apr. 1, 2004.
Co-pending U.S. Appl. No. 10/814,300, filed Apr. 1, 2004.
Co-pending U.S. Appl. No. 10/814,335, filed Apr. 1, 2004.
Co-pending U.S. Appl. No. 10/814,428, filed Apr. 1, 2004
Co-pending U.S. Appl. No. 10/814,236, filed Apr. 1, 2004.
Co-pending U.S. Appl. No. 10/814,338, filed Apr. 1, 2004.
Co-pending U.S. Appl. No. 10/814,337, filed Apr. 1, 2004.
Co-pending U.S. Appl. No. 10/814,585, filed Apr. 1, 2004.
Co-pending U.S. Appl. No. 10/742,995, filed Dec. 23, 2003.
Co-pending U.S. Appl. No. 10/814,336, filed Apr. 1, 2004.
English Language Derwent Abstract of DE 101 41 683.
English Language Derwent Abstract of DE 101 48 844.
English Language Derwent Abstract of DE 199 23 438.
English Language Derwent Abstract of DE 33 133 32.
English Language Derwent Abstract of EP 0 080 976.
English Language Derwent Abstract of EP 0 087 060.
English Language Derwent Abstract of EP 1 023 891.
English Language Derwent Abstract of EP 1 099 437.
English Language Derwent Abstract of FR 2,773,864.
English Language Derwent Abstract of FR 2,797,877.
English Language Derwent Abstract of FR 2,800,612.
English Language Abstract of FR 2 598 476 (EP 0 225 261) from EPO website.
English Language Derwent Abstract of JP 10-23629.
English Language Derwent Abstract of JP 11-060453.
English Language Derwent Abstract of JP 11-21214.
English Language Derwent Abstract of JP 2000-1417.
English Language Derwent Abstract of JP 2000-086472.
English Language Derwent Abstract of JP 2001-172120.
English Language Derwent Abstract of JP 2001-261534.
English Language Derwent Abstract of JP 2001-294519.
English Language Derwent Abstract of JP 2001-516701.
English Language Derwent Abstract of JP 2001-516706.
English Language Derwent Abstract of JP 2001-516707.
English Language Derwent Abstract of JP 2002-226338.
English Language Abstract of JP 2002-47151 from Aurigin database.
English Language Abstract of JP 2002-249419 from Japio database.
English Language Derwent Abstract of JP 2004-59468.
English Language Derwent Abstract of JP 2-200612.
English Language Derwent Abstract of JP 6-183935.
English Language Derwent Abstract of JP 6-227954.
English Language Derwent Abstract of JP 8-183716.
English Language Derwent Abstract of JP 8-208448.
French Search Report for French Patent Application No. FR 03/04021, priority document for U.S. Appl. No. 10/814,337, Dec. 8, 2003, Examiner A. Lindner.
French Search Report for French Patent Application No. FR 03/04022, priority document for co-pending U.S. Appl. No. 10/814,336, Nov. 20, 2003, Examiner A. Lindner.
French Search Report for French Patent Application No. FR 03/04024, priority document for co-pending U.S. Appl. No. 10/814,585, Dec. 8, 2003, Examiner A. Lindner.
French Search Report for French Patent Application No. FR 03/04026, priority document for co-pending U.S. Appl. No. 10/814,335, Nov. 21, 2003, Examiner T. Saunders.
French Search Report for French Patent Application No. FR 03/04027, priority document for co-pending U.S. Appl. No. 10/814,428, Nov. 28, 2003, Examiner A. Lindner.

French Search Report for French Patent Application No. FR 03/04028, priority document for co-pending U.S. Appl. No. 10/814,236, Nov. 25, 2003, Examiner T. Saunders.

French Search Report for French Patent Application No. FR 03/04029, priority document for co-pending U.S. Appl. No. 10/814,430, Feb. 5, 2004, Examiner D. Krische.

French Search Report for French Patent Application No. FR 03/04030, priority document for co-pending U.S. Appl. No. 10/814,300, Nov. 27, 2003, Examiner A. Lindner.

French Search Report for French Patent Application No. FR 03/04031, priority document for co-pending U.S. Appl. No. 10/814,333, Jan. 8, 2004, Examiner A. Lindner.

French Search Report for French Patent Application No. FR 03/04033, priority document for co-pending U.S. Appl. No. 10/814,334, Nov. 28, 2003, Examiner A. Lindner.

French Search Report for French Patent Application No. FR 03/04034, priority document for co-pending U.S. Appl. No. 10/814,338, Feb. 17, 2004, Examiner J-F. Glikman.

French Search Report for French Patent Application No. FR 03/04035, priority document for co-pending U.S. Appl. No. 10/814,305, Feb. 5, 2004, Examiner D. Krische.

French Search Report for French Patent Application No. FR 02/16669, priority document for co-pending U.S. Appl. No. 10/742,995, Aug. 6, 2003, Examiner S. Grillenberger.

International Search Report for PCT Application No. PCT/FR 02/03252, (for co-pending U.S. Appl. No. 10/490,869, Jan 20, 2003, Examiner J. F. Glikman.

Office Action mailed Nov. 17, 2005 in co-pending U.S. Appl. No. 10/814,336, Examiner E. Elhilo.

Office Action mailed Mar. 15, 2005 in co-pending U.S. Appl. No. 10/814,305, Examiner E. Elhilo.

Office Action mailed Mar. 23, 2006 in co-pending U.S. Appl. No. 10/814,300, Examiner E. Elhilo.

Office Action mailed Nov. 2, 2005 in co-pending U.S. Appl. No. 10/814,338, Examiner E. Elhilo.

Office Action mailed Nov. 2, 2005 in co-pending U.S. Appl. No. 10/742,995, Examiner E. Elhilo.

Jacobi, Otto and Jacobi, Gertrud, "Investigation into the reciprocal action of cosmetics and the biosphere of the stratum corneuum of the skin," *Cosmetics and Toiletries*, 91:25-32 (Jan. 1976).

Science Des Traitements Capillaires [Hair Treatment Sciences] by Charles Zviak, 1988, published by Masson, pp. 215 and 278.

M. Schlossmann, "The Chemistry and Manufacture of Cosmetics Formulating," 2(3):522-526 (2000).

C. D. Williams et al., "Chemistry and Technology of the Cosmetics and Toiletries Industry," ed. 2, pp. 77-78 (1996).

Yuuki Kagoubutsu Jilen (Dictionary of Organic Compounds), Kodansha Ltd., Aug. 10, 2002, p. 908.

G. Gonnum, J. Bakke and Fk. Hansen—Colloid Polym. Sci 271, 380-389 (1993).

Zviak, C., The Science of Hair Care, pp. 215 and 278 (1986).

\* cited by examiner

DYEING COMPOSITION WITH A LIGHTENING EFFECT FOR HUMAN KERATIN MATERIALS COMPRISING AT LEAST ONE FLUORESCENT DYE

The invention relates to a cosmetic composition for dyeing, with a lightening effect, human keratin materials and more particularly artificially dyed or pigmented hair and dark skin, comprising at least one fluorescent dye. The invention also relates to the processes and device using these compositions.

It is common for individuals with dark skin to wish to lighten their skin and for this purpose to use cosmetic or dermatological compositions containing bleaching agents.

The substances most commonly used as bleaching agent are hydroquinone and its derivatives, kojic acid and its derivatives, azelaic acid, arbutin and its derivatives, alone or in combination with other active agents.

However, these agents are not without their drawbacks. In particular, they need to be used for a long time and in large amounts in order to obtain a bleaching effect on the skin. No immediate effect is observed on applying compositions comprising them.

In addition, hydroquinone and its derivatives are used in an amount that is effective to produce a visible bleaching effect. In particular, hydroquinone is known for its cytotoxicity toward melanocyte.

Moreover, kojic acid and its derivatives have the drawback of being expensive and consequently of not being able to be used in large amount in products for commercial mass distribution.

There is thus still a need for cosmetic compositions that allow a lighter, uniform, homogeneous skin tone of natural appearance to be obtained, these compositions having satisfactory transparency after application to the skin.

In the field of haircare, there are mainly two major types of hair dyeing.

The first is semi-permanent dyeing or direct dyeing, which uses dyes capable of giving the hair's natural color a more or less pronounced modification that withstands shampooing several times. These dyes are known as direct dyes and may be used in two different ways. The colorations may be performed by applying the composition containing the direct dye(s) directly to the keratin fibers, or by applying a mixture, prepared extemporaneously, of a composition containing the direct dye(s) with a composition containing an oxidizing bleaching agent, which is preferably aqueous hydrogen peroxide solution. Such a process is then termed "lightening direct dyeing".

The second is permanent dyeing or oxidation dyeing. This is performed with "oxidation" dye precursors, which are colorless or weakly colored compounds which, once mixed with oxidizing products, at the time of use, can give rise to colored compounds and dyes via a process of oxidative condensation. It is often necessary to combine one or more direct dyes with the oxidation bases and couplers in order to neutralize or attenuate the shades with too much of a red, orange or golden glint or, on the contrary, to accentuate these red, orange or golden glints.

Among the available direct dyes, nitrobenzene direct dyes are not sufficiently strong, and indoamines, quinone dyes and natural dyes have low affinity for keratin fibers and consequently lead to colorations that are not sufficiently fast with respect to the various treatments to which the fibers may be subjected, and in particular with respect to shampooing.

In addition, there is a need to obtain a lightening effect on human keratin fibers. This lightening is conventionally obtained via a process of bleaching the melanins of the hair via an oxidizing system generally consisting of hydrogen peroxide optionally combined with persalts. This bleaching system has the drawback of degrading the keratin fibers and of impairing their cosmetic properties.

The Applicant thus investigated compounds that can provide solutions to the problems mentioned above, i.e. that have good dyeing affinity for keratin fibers, good fastness properties with respect to external agents, and in particular with respect to shampooing, and that also allow lightening to be obtained without impairing the fiber.

As a result of these investigations, the Applicant has now discovered, surprisingly and unexpectedly, that the use of fluorescent dyes and in particular those in the orange range allow these objectives to be achieved.

The literature discloses hair or skin compositions comprising optical brighteners or fluorescent brighteners, as described in Canadian patent 1 255 603 or patent applications WO-99/13845 and WO-00/71085. Compositions for dyeing the hair with compounds that allow strong shades to be obtained are also known, for instance those described in patent applications WO-01/62759, DE-100 29 441 and DE-199 26 377. However, these compositions do not lighten the hair or the skin at the same time as dyeing them.

Patent applications EP-0 370 470 and EP-0 445 342 describe cosmetic compositions comprising an insoluble pigment that may be fluorescent (EP-0 370 470) formed by dissolving a dye in a resin. Such compositions are not lightening.

Moreover, patents U.S. Pat. No. 5,356,438 and U.S. Pat. No. 5,188,639 describe compositions for dyeing and conditioning the hair or for dyeing and permanent-waving the hair; however, they are not intended to lighten the hair while dyeing it.

A first subject of the present invention is thus a cosmetic composition for dyeing human keratin materials with a lightening effect, characterized in that it comprises, in a cosmetically acceptable medium, at least one fluorescent dye that is soluble in the medium, which re-emits the light that it has absorbed in the visible region and also possibly in the ultraviolet region of the spectrum, as fluorescent light of a longer wavelength in the visible region of the spectrum.

For the purposes of the present invention, the term "fluorescent dye" means a dye which is a molecule that colors by itself, like any conventional dye, and a dye which is soluble in the cosmetic medium and absorbs light in the visible spectrum and possibly in the ultraviolet spectrum (wavelengths ranging from 360 to 760 nanometers), but which, in contrast to a standard dye, converts the absorbed energy into fluorescent light of a longer wavelength emitted in the visible region of the spectrum.

A fluorescent dye according to the invention is to be distinguished from an optical brightener. Optical brighteners, which are also known as brighteners, fluorescent brighteners, fluorescent brightening agents, fluorescent whitening agents, whiteners or fluorescent whiteners, are colorless transparent compounds, which do not dye because they do not absorb light in the visible region, but only in the ultraviolet region (wavelengths ranging from 200 to 400 nanometers), and convert the absorbed energy into fluorescent light of a longer wavelength emitted in the visible region of the spectrum; the color impression is then generated solely by purely fluorescent light that is predominantly blue (wavelengths ranging from 400 to 500 nanometers).

According to the present invention, the term "human keratin materials" means the skin, the hair, the nails, the eyelashes and the eyebrows, and more particularly dark skin and artificially colored or pigmented hair.

For the purposes of the invention, the term "dark skin" means a skin whose lightness L* measured in the CIEL L*a*b* system is less than or equal to 45 and preferably less than or equal to 40, given that L*=0 is equivalent to black and L*=100 is equivalent to white. The skin types corresponding to this lightness are African skin, afro-American skin, hispano-American skin, Indian skin and North African skin.

For the purposes of the invention, the expression "artificially dyed or pigmented hair" means hair whose tone height is less than or equal to 6 (dark blond) and preferably less than or equal to 4 (chestnut-brown).

The lightening of the hair is evaluated by the "tone height", which characterizes the degree or level of lightening. The notion of "tone" is based on the classification of the natural shades, one tone separating each shade from the shade immediately following or preceding it. This definition and the classification of the natural shades are well known to hairstyling professionals and are published in the book "Sciences des traitements capillaires [Hair treatment sciences]" by Charles Zviak, 1988, published by Masson, pp. 215 and 278.

The tone heights range from 1 (black) to 10 (light light blond), one unit corresponding to one tone; the higher the figure, the lighter the shade.

The fluorescent dye according to the invention should be distinguished from the fluorescent pigment. The pigment is insoluble in the medium, whereas the dye is soluble in the cosmetic medium at room temperature of about 15 to 25° C. In addition, the fluorescent dye according to the invention is a dye that generates fluorescence on the cosmetic support.

A subject of the invention is, more particularly, a cosmetic composition for dyeing human keratin materials with a lightening effect, characterized in that it comprises, in a cosmetically acceptable medium, a sufficient amount of at least one fluorescent dye, such that, after application to said materials, the composition gives a reflectance, measured at between 500 and 700 nm, which is higher than the reflectance of said untreated keratin materials.

A subject of the invention is, more particularly, a cosmetic composition for dyeing, with a lightening effect, artificially dyed or pigmented hair with a tone height of less than or equal to 6 and preferably less than or equal to 4, and also characterized in that it comprises, in a cosmetically acceptable medium, a sufficient amount of at least one fluorescent dye, such that, after application to the hair, the composition gives a reflectance, measured at between 500 and 700 nm, which is at least 0.05% and preferably at least 0.1% higher than the reflectance of the untreated hair.

Such a composition according to the invention has the advantage of lightening the hair without degrading it and of simultaneously dyeing it.

According to the present invention, the fluorescent dye, which is optionally neutralized, is soluble in the cosmetic medium to at least one gram per liter and preferably to at least five grams per liter at a temperature of 25° C.

Preferably, according to the invention, the fluorescent dye is not a fluorescein dye or a xanthene derivative as described in patent application DE-199 26 377, or a cyclopentaquinoxalinium compound as described in patent application DE-100 29 441, since these compounds are not without toxicology.

In addition, and preferably, the composition according to the invention is capable of lightening the hair and the skin in a shade which, measured in the CIEL L*a*b* system, has a variable b* of greater than or equal to 6, with a b*/absolute value of a* ratio of greater than 1.2 according to the selection test described below.

Selection Test

The composition is applied to chestnut-brown hair, at a rate of 10 grams of composition per 1 gram of chestnut-brown hair. The composition is spread on so as to cover all of the hair. The composition is left to act for 20 minutes at room temperature (20 to 25° C.). The fibers are then rinsed with water and then washed with a shampoo based on lauryl ether sulfate. They are then dried. The spectrocolorimetric characteristics of the hair are then measured in order to determine the L*a*b* coordinates.

In the CIEL L*a*b* system, a* and b* indicate two color axes: a* indicates the green/red color axis (+a* is red, −a* is green) and b* indicates the blue/yellow color axis (+b* is yellow and −b* is blue); values close to zero for a* and b* correspond to gray shades.

The fluorescent dyes preferably used according to the present invention are dyes in the orange range.

Preferably, after application to the hair, for example chestnut-brown hair, the composition should give the following results:

Attention is focused on the reflectance qualities of the hair when it is irradiated with visible light in the wavelength range from 400 to 700 nanometers.

Thus, the curves of reflectance as a function of the wavelength are compared for hair treated with the composition of the invention and untreated hair. The curve corresponding to the treated hair should show a reflectance in the wavelength range from 500 to 700 nanometers that is higher than the curve corresponding to the untreated hair.

This means that, in the wavelength range from 540 to 700 nanometers, there is at least one range in which the reflectance curve corresponding to the treated hair is higher than the reflectance curve corresponding to the untreated hair.

The term "higher than" means a difference of at least 0.05% and preferably of at least 0.1% of reflectance. This does not prevent the possibility of existence, in the wavelength range from 540 to 700 nanometers, of at least one region in which the reflectance curve corresponding to the treated hair is superimposable or lower than the reflectance curve corresponding to the untreated hair.

Preferably, the wavelength at which the difference is maximal between the reflectance curve for the treated hair and that for the untreated hair is in the wavelength range from 500 to 650 nanometers and preferably in the wavelength range from 550 to 620 nanometers.

A subject of the invention is also the use of a fluorescent dye as a lightening and dyeing agent in, or for the manufacture of, a cosmetic composition as defined above, to lighten while dyeing human keratin materials, in particular dark skin and more particularly artificially dyed or pigmented hair.

The fluorescent dyes according to the present invention are known and commercialized compounds.

Mention may especially be made among these dyes of:
the Photosensitizing Dye NK-557 sold by the company Ubichem, which has the following structure:

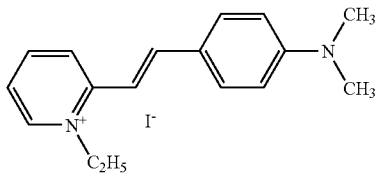

2-[2-(4-dimethylamino)phenylethenyl]-1-ethylpyridinium iodide;

Brilliant Yellow B6GL sold by the company Sandoz and having the following structure:

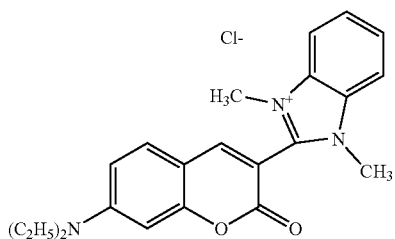

Basic Yellow 2, or Auraminoe 0, sold by the companies Prolabo, Aldrich or Carlo Erba and having the following structure:

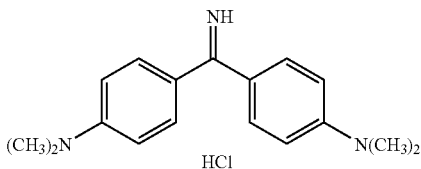

4,4'-(imidocarbonyl)bis(N,N-dimethylaniline)monohydrochloride —CAS number 2465-27-2.

The fluorescent dye(s) of the present invention preferably represent(s) from 0.01% to 20%, more preferably from 0.05% to 10% and even more particularly from 0.1% to 5% by weight approximately relative to the total weight of the composition.

The cosmetically acceptable medium generally consists of water or of a mixture of water and of at least one organic solvent.

Examples of organic solvents that may be mentioned include $C_1$–$C_4$ lower alkanols such as ethanol and isopropanol; glycerol; glycols and glycol ethers, for instance 2-butoxyethanol, propylene glycol, propylene glycol monomethyl ether, diethylene glycol monomethyl ether and monoethyl ether, and also aromatic alcohols, for instance benzyl alcohol or phenoxyethanol, similar products and mixtures thereof.

The solvents may be present in proportions preferably ranging from 1% to 40% by weight approximately and even more preferably from 5% to 30% by weight approximately relative to the total weight of the dye composition.

The pH of the composition in accordance with the invention is generally between 3 and 12 approximately and preferably between 5 and 11 approximately. It may be adjusted to the desired value by means of acidifying or basifying agents usually used in the dyeing of human keratin fibers.

Examples of acidifying agents that may be mentioned include mineral or organic acids, for instance hydrochloric acid, orthophosphoric acid, sulfuric acid, carboxylic acids, for instance acetic acid, tartaric acid, citric acid and lactic acid, and sulfonic acids.

Examples of basifying agents that may be mentioned include aqueous ammonia, alkaline carbonates, alkanolamines such as monoethanolamine, diethanolamine and triethanolamine and derivatives thereof, sodium hydroxide, potassium hydroxide and the compounds of formula (I) below:

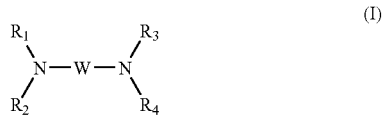

in which W is a propylene residue optionally substituted with a hydroxyl group or a $C_1$–$C_6$ alkyl radical; $R_1$, $R_2$, $R_3$ and $R_4$, which may be identical or different, represent a hydrogen atom or a $C_1$–$C_6$ alkyl or $C_1$-$C_6$ hydroxyalkyl radical.

According to one preferred embodiment, the cosmetic composition in accordance with the invention may comprise, in addition to the fluorescent dye(s), one or more additional direct dyes of nonionic, cationic or anionic nature, which may be chosen, for example, from the following red or orange nitrobenzene dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)-benzene,
1-(β,γ-dihydroxypropyl)oxy-3-nitro-4-(β-hydroxyethyl)-aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine and
1-amino-2-nitro-4-hydroxy-5-methylbenzene.

The cosmetic composition in accordance with the invention may also comprise, in addition to or in replacement for these nitrobenzene dyes, one or more additional direct dyes chosen from yellow, green-yellow, blue or violet nitrobenzene dyes, azo dyes, anthraquinone dyes, naphthoquinone dyes, benzoquinone dyes, indigoid dyes, and triarylmethane-based dyes.

These additional direct dyes may especially be basic dyes, among which mention may be made more particularly of the dyes known in the Color Index, 3rd edition, under the names "Basic Brown 16", "Basic Brown 17", "Basic Yellow 57", "Basic Red 76", "Basic Violet 10", "Basic Blue 26" and "Basic Blue 99", or acidic direct dyes, among which mention may be made more particularly of the dyes known in the Color Index, 3rd edition, under the names "Acid Orange 7", "Acid Orange 24", "Acid Yellow 36", "Acid Red 33", "Acid Red 184", "Acid Black 2", "Acid Violet 43" and "Acid Blue 62", or alternatively cationic direct dyes such as those described in WO 95/01772, WO 95/15144 and EP-A-0 714 954, the content of which forms an integral part of the present invention.

Among the additional yellow and green-yellow nitrobenzene direct dyes that may be mentioned, for example, are the compounds chosen from:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene and
4-(β-hydroxyethyl)amino-3-nitrobenzamide.

Among the additional blue or violet nitrobenzene direct dyes that may be mentioned, for example, are the compounds chosen from:
1-(β-hydroxyethyl)amino-4-N,N-bis(β-hydroxyethyl)amino-2-nitrobenzene,
1-(γ-hydroxypropyl)amino-4,N,N-bis(β-hydroxyethyl)amino-2-nitrobenzene,
1-(β-hydroxyethyl)amino-4-(N-methyl-N-β-hydroxy-ethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitro-para-phenylenediamines having the following formula (II):

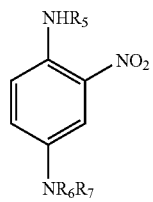

(II)

in which:
R₆ represents a $C_1$–$C_4$ alkyl radical or a β-hydroxy-ethyl, β-hydroxypropyl or γ-hydroxypropyl radical;
R₅ and R₇, which may be identical or different, represent a β-hydroxyethyl, β-hydroxypropyl, γ-hydroxypropyl or β,γ-dihydroxypropyl radical, at least one of the radicals R₆, R₇ or R₅ representing a γ-hydroxypropyl radical and R₆ and R₇ not simultaneously being able to denote a β-hydroxyethyl radical when R₆ is a γ-hydroxypropyl radical, such as those described in FR 2 692 572.

When they are present, the additional direct dye(s) preferably represent(s) from 0.0005% to 12% by weight approximately relative to the total weight of the composition, and even more preferably from 0.005% to 6% by weight approximately relative to this weight.

When it is intended for oxidation dyeing, the cosmetic composition in accordance with the invention comprises, in addition to the fluorescent compound(s), at least one oxidation base chosen from the oxidation bases conventionally used for oxidation dyeing and among which mention may be made especially of para-phenylenediamines, bis(phenyl)alkylenediamines, para-aminophenols, ortho-aminophenols and heterocyclic bases, and the addition salts thereof with an acid or with an alkaline agent.

Among the para-phenylenediamines that may be mentioned more particularly, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy)pyrrolidine, and the addition salts thereof with an acid or with an alkaline agent.

Among the para-phenylenediamines mentioned above, the ones most particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid or with an alkaline agent.

Among the bis(phenyl)alkylenediamines that may be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid or with an alkaline agent.

Among the para-aminophenols that may be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

Among the ortho-aminophenols that may be mentioned more particularly, for example, are 2-aminophenol, 2-amino-5-methylphenol, 2-amino-6-methylphenol and 5-acetamido-2-aminophenol, and the addition salts thereof with an acid or with an alkaline agent.

Among the heterocyclic bases that may be mentioned more particularly, for example, are pyridine derivatives, pyrimidine derivatives and pyrazole derivatives, and the addition salts thereof with an acid or with an alkaline agent.

When they are used, the oxidation base(s) advantageously represent(s) from 0.0005% to 12% by weight relative to the total weight of the composition and even more preferably from 0.005% to 6% by weight approximately relative to this weight.

When it is intended for oxidation dyeing, the cosmetic composition in accordance with the invention may also comprise, in addition to the fluorescent dyes and the oxidation bases, at least one coupler so as to modify or to enrich with glints the shades obtained using the fluorescent dyes and the oxidation base(s).

The couplers that may be used in the cosmetic composition in accordance with the invention may be chosen from the couplers conventionally used in oxidation dyeing, and among which mention may be made especially of meta-phenylenediamines, meta-aminophenols, meta-diphenols and heterocyclic couplers, and the addition salts thereof with an acid or with an alkaline agent.

These couplers are more particularly chosen from 2-methyl-5-aminophenol, 5-N-(5-hydroxyethyl)amino-2-methylphenol, 3-aminophenol, 1,3-dihydroxybenzene, 1,3-dihydroxy-2-methylbenzene, 4-chloro-1,3-dihydroxy-benzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, and the addition salts thereof with an acid or with an alkaline agent.

When they are present, the coupler(s) preferably represent(s) from 0.0001% to 10% by weight and even more preferably from 0.005% to 5% by weight relative to the total weight of the composition.

In general, the addition salts with an acid that may be used in the context of the compositions of the invention (oxidation bases and couplers) are chosen especially from the hydrochlorides, hydrobromides, sulfates, citrates, succinates, tartrates, tosylates, benzenesulfonates, lactates and acetates.

The addition salts with an alkaline agent that may be used in the context of the compositions of the invention (oxidation bases and couplers) are chosen especially from the addition salts with alkali metals or alkaline-earth metals, with ammonia and with organic amines, including alkanolamines and the compounds of formula (I).

The cosmetic composition in accordance with the invention may also comprise various adjuvants conventionally used in cosmetic compositions, in particular for dyeing human keratin fibers, such as anionic, cationic, nonionic, amphoteric or zwitterionic surfactants or mixtures thereof, anionic, cationic, nonionic, amphoteric or zwitterionic polymers, or mixtures thereof, mineral or organic thickeners, antioxidants, penetrating agents, sequestering agents, fragrances, buffers, dispersants, conditioners, for instance cations, cationic or amphoteric polymers, volatile or nonvolatile, modified or unmodified silicones, film-forming agents, ceramides, preserving agents, stabilizers and opacifiers.

Among the thickeners that it is more particularly preferred to use are thickening systems based on associative polymers that are well known to those skilled in the art and especially of nonionic, anionic, cationic or amphoteric nature.

Needless to say, a person skilled in the art will take care to select this or these optional additional compound(s) such that the advantageous properties intrinsically associated with the composition in accordance with the invention are not, or are not substantially, adversely affected by the envisaged addition(s).

The cosmetic composition according to the invention may be in various forms, such as in the form of liquids, shampoos, creams or gels, or in any other suitable form.

One form that is particularly preferred according to the present invention, and which constitutes another subject of the invention, is a lightening and dyeing shampoo comprising, in a cosmetically acceptable aqueous medium, at least one fluorescent dye as defined above, and at least one surfactant, which is preferably nonionic.

In these shampoos, the surfactants are present in a proportion ranging from about 4% to 30% and preferably from about 8% to 20% by weight relative to the total weight of the shampoo composition, and the nonionic surfactants that are more particularly preferred are chosen from alkylpolyglucosides.

In the composition according to the invention, when one or more oxidation bases are used, optionally in the presence of one or more couplers, or when the fluorescent dye(s) is (are) used in the context of a lightening direct dyeing operation, then the composition in accordance with the invention may also contain at least one oxidizing agent chosen, for example, from hydrogen peroxide, urea peroxide, alkali metal bromates, persalts such as perborates and persulfates, and enzymes such as peroxidases and two-electron or four-electron oxidoreductases. The use of hydrogen peroxide or of enzymes is particularly preferred.

Another subject of the invention is a process for dyeing and lightening the hair, using a composition as defined above, in the absence of oxidation dyes and of oxidizing agents.

Another subject of the invention is a process for dyeing the hair using a composition as defined above, in the absence of oxidation dyes but in the presence of oxidizing agents.

According to a first variant of these dyeing processes in accordance with the invention, at least one composition as defined above is applied to the hair, for a time that is sufficient to develop the desired coloration and lightening, after which the hair is rinsed, optionally washed with shampoo, rinsed again and dried.

According to a second variant of these dyeing processes in accordance with the invention, at least one composition as defined above is applied to the hair, for a time that is sufficient to develop the desired coloration and lightening, without final rinsing.

According to a third variant of the dyeing process in accordance with the invention, the dyeing process comprises a preliminary step that consists in separately storing, on the one hand, a composition comprising, in a medium that is suitable for dyeing, at least one fluorescent dye, and, on the other hand, a composition comprising, in a medium that is suitable for dyeing, at least one oxidizing agent, and then in mixing them together at the time of use, followed by applying this mixture to the hair for a time that is sufficient to develop the desired coloration, after which the hair is rinsed, optionally washed with shampoo, rinsed again and dried.

Another subject of the invention is a process for the oxidation dyeing of the hair using a composition as defined above in the presence of oxidation dyes.

According to this dyeing process, the dyeing process comprises a preliminary step that consists in separately storing, on the one hand, a composition comprising, in a medium that is suitable for dyeing, at least one fluorescent dye and at least one oxidation base, and, on the other hand, a composition comprising, in a medium that is suitable for dyeing, at least one oxidizing agent, and then in mixing them together at the time of use, followed by applying this mixture to the hair for a time that is sufficient to develop the desired coloration, after which the hair is rinsed, optionally washed with shampoo, rinsed again and dried.

Another subject of the invention is a multi-compartment device for dyeing and lightening the hair, comprising at least one compartment containing a composition comprising at least one fluorescent dye, and at least one other compartment containing a composition comprising at least one oxidizing agent. This device may be equipped with a means for applying the desired mixture to the hair, such as the devices described in patent FR-2 586 913 in the name of the Applicant.

A subject of the invention is also a process that consists in applying the composition according to the invention to hair with a tone height of less than or equal to 6 and preferably less than or equal to 4.

The time required to develop the coloration and to obtain the lightening effect on the hair is from about 5 to 60 minutes and more particularly from about 5 to 40 minutes.

The temperature required to develop the coloration and to obtain the lightening effect on the hair is generally between room temperature (15 to 25° C.) and 80° C. and more particularly between 15 and 40° C.

Another subject of the invention is a process for lightening skin whose lightness L* in the CIEL L*a*b* system is less than or equal to 45 and preferably less than or equal to 40, which consists in applying to the skin a composition in accordance with the invention and as described above.

The examples that follow are intended to illustrate the invention without, however, limiting its scope.

EXAMPLES 1 to 5

The 3 direct dyeing compositions below according to the invention were prepared (contents in grams):

| EXAMPLES according to the invention | 1 | 2 | 3 |
|---|---|---|---|
| Fluorescent dye NK-557 | 0.5 | — | — |
| Fluorescent dye Brilliant Yellow B6GL | | 0.5 | |
| Fluorescent dye Basic Yellow 2 | | | 0.5 |
| Hydroxyethylcellulose | 1.6 | 1.6 | 1.6 |
| (50/50 C8/C10)alkyl polyglucoside as a buffered 60% aqueous solution | 6 AM* | 6 AM* | 6 AM* |
| Benzyl alcohol | 8 | 8 | 8 |
| Polyethylene glycol | 12 | 12 | 12 |
| Mixture of methyl, butyl, ethyl, propyl and isobutyl p-hydroxybenzoates | 0.12 | 0.12 | 0.12 |
| Demineralized water qs | 100 | 100 | 100 |

AM* denotes Active Material

Two comparative compositions, not in accordance with the invention, having the same composition as the above three compositions according to the invention, with the exception of the dye, which is also orange but is non-fluorescent, were also prepared:

| Comparative Examples not in accordance with the invention | 4 | 5 |
|---|---|---|
| Non-fluorescent dye ♦ | 0.5 | |
| Non-fluorescent dye ♦♦ | | 0.5 |
| Hydroxyethylcellulose | 1.6 | 1.6 |
| (50/50 C8/C10)alkyl polyglucoside as a buffered 60% aqueous solution | 6 AM* | 6 AM* |
| Benzyl alcohol | 8 | 8 |
| Polyethylene glycol | 12 | 12 |
| Mixture of methyl, butyl, ethyl, propyl and isobutyl p-hydroxybenzoates | 0.12 | 0.12 |
| Demineralized water qs | 100 | 100 |

AM* denotes Active Material
♦ 2-nitro-4-hydroxy-1-aminobenzene
♦♦ Basic Orange 31 or Vibracolor flame orange sold by the company Ciba Geigy, having the following formula:

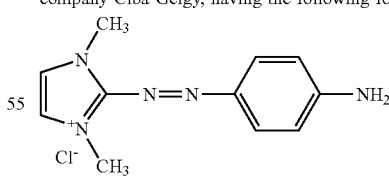

Each composition 1 to 5 was applied, at a rate of 10 grams each, to 1 g of locks of chestnut-brown natural hair and was left to act for 20 minutes. The locks were then rinsed with water and then dried.

After 24 hours, the locks were read using a Minolta CM 2002 calorimeter in the L*A*b* system, and the tone heights were evaluated.

The results are collated in table (I) below:

|  | TH* | L* | a* | b* | b*/a* |
|---|---|---|---|---|---|
| Non-dyed control | 4 | 24.24 | 3.82 | 4.51 | 1.18 |
| Composition 1 | 5 | 26.77 | 5.61 | 8.41 | 1.50 |
| Composition 2 | 4.5 | 25.85 | −1.07 | 8.92 | 8.34 |
| Composition 3 | 5 | 24.76 | 1.61 | 6 | 3.73 |
| Composition 4 | 4 | 23.99 | 6.43 | 5.71 | 0.89 |
| Composition 5 | 4 | 23.25 | 6.84 | 4.44 | 0.65 |

TH* denotes Tone Height

From these results it is clearly seen that only the three compositions 1 to 3 according to the invention color the hair while lightening it.

Moreover, the differences in reflectance between the untreated chestnut-brown hair and the chestnut-brown hair treated with each of the above compositions 1 to 5 were as follows:

| Composition | Wavelength in nanometers | Difference in reflectance, in % |
|---|---|---|
| 1 | 580 | 1.49 |
| 2 | 550 | 0.17 |
| 3 | 550 | 0.33 |
| 4 | 550 | −0.38 |
| 5 | 550 | −0.66 |

The results are given on the reflectance curves table (II) below.

The results are given on the reflectance curves in table (II) below.
Table (II)
Difference in reflectance between chestnut-brown hair and dyed chestnut-brown hair
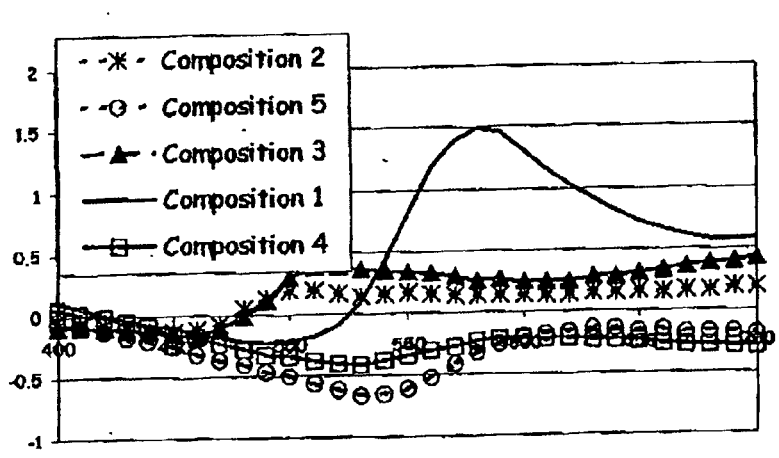

This graph shows on the x-axis the wavelength of the light illuminating the hair, and on the y-axis the difference in reflectance of the hair for each wavelength between the dyed chestnut-brown hair and the non-dyed chestnut-brown hair (tone height 4).

It is noted that, for compositions 1, 2 and 3 (with fluorescent dyes), the reflectance is positive (>0%) throughout virtually all the wavelength range, whereas, for compositions 4 and 5 (with non-fluorescent dyes), the reflectance is always negative and thus lower than the reflectance of the non-dyed chestnut-brown hair.

EXAMPLE 6

The lightening and dyeing shampoo of the composition below was prepared:

(contents expressed in grams of Active Material AM*)

| | |
|---|---|
| Nonionic surfactant: alkyl polyglucoside as an aqueous solution containing 53% AM* (Plantacare 2002 Up sold by Cognis | 15.9 AM* |
| 1,2-Pentanediol | 0.1 |
| Glycerol | 7 |
| Anisic acid | 0.2 |
| Cationic conditioner: Quaternium-87 (dimethylalkylamidoethylimidazolium methosulfate as a solution in propylene glycol or Rewoquat W 575 PG sold by Goldschmidt) | 0.15 AM* |
| Stabilizer: polyethylene glycol distearate (PEG-50 distearate) | 4.2 |
| Sodium chloride | 3 |
| Citric acid | 2.4 |
| Sodium hydroxide | 0.92 |
| Fluorescent dye NK-557 | 0.5 |
| Demineralized water qs | 100 |

Five tests of application of this shampoo to locks of chestnut-brown hair were then performed by applying the selection test described in the invention.

Tests 3 and 4 were performed to show that the shampoos can be superimposed and nevertheless lead to a simultaneous lightening and dyeing result.

Test 1: a lock of 1 gram of chestnut-brown hair was treated with 10 grams of shampoo for 20 minutes at room temperature. The lock was then rinsed with water and dried.

Test 2: a lock of 1 gram of chestnut-brown hair was treated with 0.4 gram of shampoo for one minute at room temperature. The lock was then rinsed with water and dried.

Test 3: the 1-gram lock of hair from Test 2 was again treated with 0.4 gram of shampoo for one minute at room temperature. The lock was then rinsed with water and dried.

Test 4: the 1-gram lock of hair from Test 3 was again treated with 0.4 gram of shampoo for one minute at room temperature. The lock was then rinsed with water and dried.

The locks were lightened, and the L*a*b* measurements collated in table (III) below show that the composition of example 6 satisfies the selection criteria of the present invention.

TABLE (III)

| | L* | a* | b* | b*/absolute value of a* | Wavelength in nanometers | Difference in reflectance in % |
|---|---|---|---|---|---|---|
| Control** | 22.34 | 3.14 | 3.96 | | | |
| Test 1 | 23.86 | 4.18 | 7.48 | 1.79 | 580 | 0.84 |
| Test 2 | 23.98 | 3.72 | 6.24 | 1.68 | 580 | 0.74 |
| Test 3 | 23.84 | 3.91 | 6.15 | 1.57 | 580 | 0.74 |
| Test 4 | 24.33 | 4.26 | 7.13 | 1.67 | 580 | 1.04 |

**untreated hair

The invention claimed is:

1. A process for dyeing hair having a tone height of less than or equal to 6 with a lightening effect, comprising applying to the hair, in an amount effective to provide a lightening effect on fibers that have a tone height of less than or equal to 6, a composition comprising, in a cosmetically acceptable medium, at least one fluorescent dye that is soluble in the cosmetically acceptable medium, which re-emits light that it has absorbed in the visible region of the spectrum as fluorescent light of a longer wavelength in the visible region of the spectrum;

wherein the at least one fluorescent dye is chosen from:

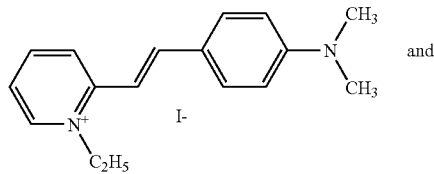

and

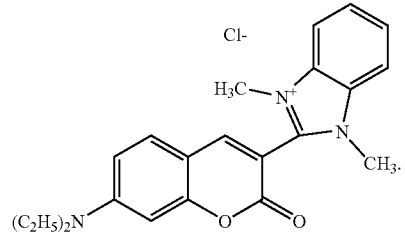

2. The process according to claim 1, wherein the at least one fluorescent dye re-emits, in addition to the light that it has absorbed in the visible region of the spectrum, the light that it has absorbed in the ultraviolet region of the spectrum as fluorescent light of a longer wavelength in the visible region of the spectrum.

3. The process according to claim 1, wherein the hair is artificially dyed or pigmented hair.

4. The process according to claim 1, wherein the hair has a tone height of less than or equal to 4.

5. The process according to claim 1, wherein the at least one fluorescent dye is present in an amount such that, after application to the hair, the composition gives a reflectance, ranging from 500 to 700 nm, which is at least 0.05% higher than the reflectance of the hair not treated with the composition.

6. The process according to claim 5, wherein the at least one fluorescent dye is present in an amount such that, after application to the hair, the composition gives a reflectance, ranging from 500 to 700 nm, which is at least 0.1% higher than the reflectance of the hair not treated with the composition.

7. The process according to claim 1, wherein the at least one fluorescent dye lightens the hair and the skin in a shade which, measured in the CIEL L*a*b* system, has a variable b* of greater than or equal to 6, with a b*/absolute value of a* ratio of greater than 1.2.

8. The process according to claim 1, wherein the at least one fluorescent dye is present in an amount ranging from 0.01% to 20% by weight, relative to the total weight of the composition.

9. The process according to claim 8, wherein the at least one fluorescent dye is present in an amount ranging from 0.05% to 10% by weight, relative to the total weight of the composition.

10. The process according to claim 9, wherein the at least one fluorescent dye is present in an amount ranging from 0.1% to 5% by weight, relative to the total weight of the composition.

11. The process according to claim 1, wherein the cosmetically acceptable medium comprises water or a mixture of water and of at least one organic solvent.

12. The process according to claim 1, wherein the composition has a pH ranging from 3 to 12.

13. The process according to claim 12, wherein the composition has a pH ranging from 5 to 11.

14. The process according to claim 1, wherein the composition further comprises at least one additional direct dye chosen from nonionic, cationic, and anionic direct dyes.

15. The process according to claim 14, wherein the at least one additional direct dye is chosen from nitrobenzene dyes.

16. The process according to claim 14, wherein the at least one additional direct dye is chosen from azo dyes, anthraquinone dyes, naphthoquinone dyes, benzoquinone dyes, indigoid dyes and triarylmethane-based dyes.

17. The process according to claim 14, wherein the at least one additional direct dye is present in an amount ranging from 0.0005% to 12% by weight, relative to the total weight of the composition.

18. The process according to claim 17, wherein the at least one additional direct dye is present in an amount ranging from 0.005% to 6% by weight, relative to the total weight of the composition.

19. The process according to claim 1, wherein the composition is in the form of a lightening and dyeing shampoo, and further comprises at least one surfactant.

20. The process according to claim 19, wherein the at least one surfactant is nonionic.

21. The process according to claim 1, wherein the composition is an oxidation dyeing composition and comprises at least one oxidation base.

22. The process according to claim 21, wherein the at least one oxidation base is chosen from para-phenylenediamines, bis(phenyl)alkylenediamines, para-aminophenols, ortho-aminophenols and heterocyclic bases, and the addition salts thereof with an acid or with an alkaline agent.

23. The process according to claim 22, wherein the at least one oxidation base is present in an amount ranging from 0.0005% to 12% by weight, relative to the total weight of the composition.

24. The process according to claim 23, wherein the at least one oxidation base is present in an amount ranging from 0.005% to 6% by weight, relative to the total weight of the composition.

25. The process according to claim 21, wherein the composition further comprises at least one coupler chosen from meta-phenylenediamines, meta-aminophenols, meta-diphenols and heterocyclic couplers, and addition salts thereof with an acid or with an alkaline agent.

26. The process according to claim 25, wherein the at least one coupler is present in an amount ranging from 0.0001% to 10% by weight, relative to the total weight of the dye composition.

27. The process according to claim 26, wherein the at least one coupler is present in an amount ranging from 0.005% to 5% by weight, relative to the total weight of the dye composition.

28. The process according to claim 1, wherein the composition further comprises at least one oxidizing agent.

29. The process according to claim 28, wherein the at least one oxidizing agent is chosen from hydrogen peroxide, urea peroxide, alkali metal bromates, persalts, and enzymes.

30. The process according to claim 29, wherein the persalts are chosen from perborates and persulfates.

31. The process according to claim 29, wherein the enzymes are chosen from peroxidases and two-electron and four-electron oxidoreductases.

32. The process according to claim 29, wherein the oxidizing agent is hydrogen peroxide.

33. A multi-compartment device for dyeing and lightening the hair, comprising at least one first compartment comprising at least one cosmetic composition for dyeing hair having a tone height of less than or equal to 6 with a lightening effect, comprising, in a cosmetically acceptable medium, at least one fluorescent dye that is soluble in the cosmetically acceptable medium, which re-emits light that it has absorbed in the visible region of the spectrum as fluorescent light of a longer wavelength in the visible region of the spectrum, and comprising at least one second compartment comprising at least one composition comprising at least one oxidizing agent;

wherein the at least one fluorescent dye is chosen from:

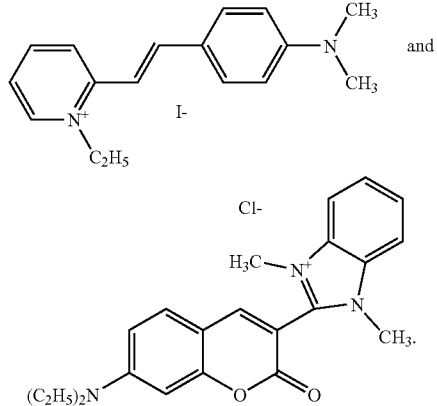

34. The device according to claim 33, wherein the at least one fluorescent dye re-emits, in addition to the light that it has absorbed in the visible region of the spectrum, the light that it has absorbed in the ultraviolet region of the spectrum as fluorescent light of a longer wavelength in the visible region of the spectrum.

* * * * *